United States Patent [19]

Noda et al.

[11] 4,083,994
[45] Apr. 11, 1978

[54] CHOLERETICS

[75] Inventors: Kanji Noda, Chikushino; Ryuhei Kodama, Tosu; Tadanori Yano, Tosu; Hideaki Inoue, Tosu; Kazuhide Furukawa, Tosu; Hirotsune Igimi, Fukuoka; Hiroyuki Ide, Fukuoka, all of Japan

[73] Assignee: Hisamitsu Pharmaceutical Co., Inc., Tosu, Japan

[21] Appl. No.: 710,474

[22] Filed: Aug. 2, 1976

[30] Foreign Application Priority Data

Aug. 30, 1975  Japan ................... 50-105451

[51] Int. Cl.² ............... A61K 31/22; A61K 31/045; A61K 31/015
[52] U.S. Cl. .................... 424/311; 424/343; 424/356
[58] Field of Search .......... 424/356, 311, 84; 260/489; 560/249; 426/538

[56] References Cited

U.S. PATENT DOCUMENTS

| | | | |
|---|---|---|---|
| 2,312,684 | 3/1943 | Borglin | 260/489 |
| 2,312,685 | 3/1943 | Borglin | 260/489 |
| 2,423,545 | 7/1947 | Aeschbach | 260/489 |
| 2,501,199 | 3/1950 | Wearn et al. | 260/489 |
| 2,803,647 | 8/1957 | Bain et al. | 260/489 |
| 3,014,047 | 12/1961 | Bain et al. | 260/489 |

OTHER PUBLICATIONS

Chemical Abstracts: vol. 49: 6887h–6888a, (1955); vol. 65:10626e, (1966) & vol. 66:9112h (1967), & Index p. 4252f.

*Primary Examiner*—Donald B. Moyer
*Attorney, Agent, or Firm*—Browdy and Neimark

[57] ABSTRACT

Choleretics which include, as effective ingredients, one or more than two limonene derivatives selected from p-mentha-1,8-diene, p-menth-1-ene-8,9-diol, 9-acetoxy-p-menth-1-en-8-ol and 9-propionyloxy-p-menth-1-en-8-ol, possess a markedly high choleretic activity as compared to that of the conventional choleretics and ensure a high safety for medical use.

19 Claims, No Drawings

CHOLERETICS

DETAILED DESCRIPTION

The present invention relates to novel choleretics. More particularly, the present invention relates to choleretics comprising limonene derivatives as effective ingredients, which may stimulate the secretion of bile. Choleretics have been essential for treatment of diseases in the hepato-biliary system, and therefore various kinds of choleretics have been developed and used. For example, bile acids, turmeric, and quinophen(Trade name : Atphan) have been used for many years, and dehydrocholic acid, ursodeoxycholic acid, phenylpropanol(-Trade name : Felicur) and compounding preparations such as Rowachol(Trade name), Galle and Donau(-Trade name) are often used as recently developed choleretics. However, these choleretics are of extremely short duration of action, and often cause such side effects as gastrointestinal disorders and allergic reactions. In addition, since these choleretics have such drawbacks that they are expensive because of high cost of their raw materials and that their effective doses are very large, it is said that they are not complete medicaments as choleretics.

The occurrence of hepato-biliary diseases including cholelithiasis has a tendency to increase year by year. Consequently, the development of new choleretics possessing high efficacy and biological safety as well as low cost has been required from all quarters. The present inventors have, therefore, investigated to develop a novel choleretic. As a result of chemical studies on essential oils as well as metabolism studies on d-limonene, they have found that several well-known limonene derivatives are suitable for new choleretics, which possess a marked choleretic activity when compared with that of the conventional choleretics, and completed the present invention.

The present invention relates to choleretics which consist of one or more than two limonene derivatives selected from p-mentha-1,8-diene, p-menth-1-ene-8,9-diol, 9-acetoxy-p-menth-1-en-8-ol and 9-propionyloxy-p-menth-1-en-8-ol as effective ingredients.

As is known, a choleretic is a general term for those agents which may increase bile secretion, and in more detail, it may be divided according to its mechanism of action into two: the hydrocholeretics which increase the volume of the bile and the cholagogues which stimulate evacuation of the gallbladder. The choleretics of the present invention belong to the former.

The d-limonene derivatives of the present invention which possess high choleretic activity are oily or crystalline substances, so that they may be easily prepared into various pharmaceutical dosage forms such as capsules, granules, pills, powders, tablets, syrups, tinctures, injections and rectal suppositories using the conventional methods of manufacturing.

The said limonene derivatives may be used alone, but the following substances alone or in combination may be compounded to the said derivatives according to the pharmaceutical preparations mentioned above, using the pharmaceutically acceptable techniques: saccharides, such as glucose, sucrose, lactose, millet jelly, honey and starch; celluloses, such as methylcellulose, carboxymethylcellulose and hydroxypropyl cellulose; natural vegetable resins, such as gum arabic and tragacanth powders; glycyrrhiza powder and crude extract; gentian powder and extract; dried yeast and yeast extract; gelatin, agar powder, propylene glycol, glycerin, polyvinylpyrrolidone, distilled water, alcohol, suspending agents, emulsifiers and surfactants. In addition, cyclodextrins such as cyclohexamylose, cycloheptamylose and cyclooctamylose may be compounded to the said derivatives to make inclusion compounds. A preferred route of administration is an oral route. While a pharmaceutical preparation of the choleretics of the present invention is exemplified in the following, it is not intended that this example shall be construed to limit the scope of the present invention.

Example of pharmaceutical preparation

Ninety mg of gelatin(USP), 27 mg of glycerin(USP), 4.5 mg of sorbitol(USP), 18 mg of gum arabic(USP) and 0.23 mg of coal-tar colors were dissolved in distilled water by heating for 5–6 hours to make a gelatin mixture. Air bubbles formed in the gelatin mixture were burst by vacuum, and the mixture was made into a thin sheet. Soft elastic capsules were prepared by the plate process, using a set of molds to form the spherical capsules. A warm sheet of the gelatin mixture is laid over the lower plate and the liquid, p-mentha-1,8-diene, was evenly poured on it to contain 200 mg per capsule. A second sheet of the gelatin mixture was carefully laid in place on top of the liquid, and the top place of the mold is put in place. The entire mold is then subjected to a press where pressure is applied to form, fill and seal the capsules simultaneously. The capsules were removed, washed off with a volatile solvent and dried for 20–30 hours. Thus, the spherical capsules each containing 200 mg of p-mentha-1,8-diene could be obtained.

The other limonene derivatives of the present invention were also made into capsules according to the method mentioned above.

The doses of the said limonene derivatives which may exert a choleretic activity on humans are 150–2500 mg/day, and preferably 300–900 mg/day.

The therapeutic indications for use of the choleretics of the present invention are for hepato-biliary diseases, for example, cholecystitis, acute and chronic hepatitis, hepato-cirrhosis, hyperlipoidemia, choledochititis, acholia, jaundice and cholelithiasis.

The said limonene derivatives consist generally of a mixture of stereomers and optical isomers, and the mixture itself is enough to exert a choleretic activity. Naturally, the stereomers or optical isomers separated in a high state of purity may be used also as choleretics, but such a separation is not particularly necessary.

The limonene derivatives, which are effective ingredients of the choleretics of the present invention, possess a surprisingly high choleretic activity, which could be proved by pharmacological tests with rats and dogs. Furthermore, it is evident from the results of these tests that the volume of the bile secretion is augmented along with increasing doses of the limonene derivatives.

In the tests, well-known phenylpropanol(Trade name: Felicur), Rowachol(Trade name) and 1-menthol were selected as reference compounds or drugs. 1-Menthol alone has not been used as a choleretic. However, since 1-menthol comprises 32% of the effective ingredients of Rowachol, it must be regarded as a major component, by which the choleretic activity of Rowachol may possibly be caused. This is the reason why d-limonene itself is also selected as a reference compound in the tests.

1. Bile secretion test in rats

Male Wistar rats weighing 200–210 g were fasted overnight and laparotomized under urethane anesthesia (Subcutaneous injection at a dose of 1.5 g/kg). A polyethylene tube was inserted into the common bile duct. The bile was collected for one hour from 30 minutes after the operation. Subsequently, the animals were given orally the test drugs, each 50 mg of which was suspended in 1 ml of 5% gum arabic aqueous solution. The bile was collected for 5 hours after the drug administration. The volume of the bile secreted at hourly intervals after the drug administration was expressed in %, defining the volume secreted for one hour before the drug administration as 100%, as shown in Table 1.

The mean volume of the bile secreted for one hour before the drug administration was 872 μl.

Table 1

Effects of test drugs on bile secretion in rats

| Test Drug | Dose (mg/kg) | *Bile volume secreted before administration(%) | Bile volume secreted after administration(%) | | | | |
|---|---|---|---|---|---|---|---|
| | | | $0-1^{hr}$ | $1-2^{hr}$ | $2-3^{hr}$ | $3-4^{hr}$ | $4-5^{hr}$ |
| Control | 0 | 100 | 94 | 88 | 84 | 81 | 79 |
| Choleretics of the present invention: | | | | | | | |
| p-Mentha-1,8-diene | 80 | 100 | 101 | 100 | 100 | 94 | 91 |
| | 250 | 100 | 104 | 108 | 109 | 108 | 104 |
| | 750 | 100 | 111 | 125 | 128 | 131 | 128 |
| p-Menth-1-ene-8,9-diol | 80 | 100 | 155 | 118 | 101 | 93 | 85 |
| | 250 | 100 | 213 | 170 | 122 | 99 | 89 |
| | 750 | 100 | 218 | 199 | 175 | 153 | 139 |
| 9-Acetoxy-p-menth-1-en-8-ol | 100 | 100 | 125 | 109 | 96 | 82 | 75 |
| | 310 | 100 | 196 | 172 | 145 | 124 | 114 |
| | 930 | 100 | 218 | 203 | 172 | 154 | 130 |
| 9-Propionyloxy-p-menth-1-en-8-ol | 110 | 100 | 135 | 117 | 100 | 87 | 74 |
| | 330 | 100 | 147 | 139 | 118 | 104 | 86 |
| | 990 | 100 | 176 | 174 | 153 | 130 | 120 |
| Known choleretics: | | | | | | | |
| l-Menthol | 80 | 100 | 134 | 114 | 100 | 95 | 89 |
| | 230 | 100 | 139 | 137 | 133 | 117 | 111 |
| | 750 | 100 | 152 | 143 | 138 | 122 | 111 |
| Felicur | 250 | 100 | 204 | 172 | 138 | 108 | 88 |
| Rowachol | 250 | 100 | 136 | 123 | 109 | 102 | 98 |

*The mean volume of the bile secreted for one hour before the drug administration was 872 μl, which was defined as 100 %.

2. Bile secretion test in dogs

Male mongrel dogs weighing approximately 8 kg were anesthetized with intravenous injection of 20 mg of pentobarbital and further with subcutaneous injection of urethane at a dose of 1.0 g/kg and laparotomized. One canula was inserted into the common bile duct and directed to the liver for collection of the bile, and the other canula was inserted into the duodenum for the drug administration. The cholecystic duct was ligated and the gallbladder bile was aspirated with an injection syringe. The operation was finished by suture of the peritoneum. The bile was collected for one hour from 30 minutes after the operation. The animals were given the test drugs, each 50 mg of which was suspended in 1 ml of 5% gum arabic aqueous solution, through the canula for the drug administration. The bile was collected at hourly intervals for 6 hours after the drug administration. Defining the volume of the bile secreted for one hour before the drug administration as 100%, the volume secreted at hourly intervals after the drug administration was expressed in %, as shown in Table 2.

The mean volume secreted for one hour before the drug administration was 1798 μl.

Table 2

Effects of test drugs on bile secretion in dogs

| Test Drug | Dose (mg/kg) | *Bile volume secreted before administration(%) | Bile volume secreted after administration(%) | | | | | |
|---|---|---|---|---|---|---|---|---|
| | | | $0-1^{hr}$ | $1-2^{hr}$ | $2-3^{hr}$ | $3-4^{hr}$ | $4-5^{hr}$ | $5-6^{hr}$ |
| Control | 0 | 100 | 93 | 63 | 62 | 54 | 50 | 46 |
| Choleretics of the present invention: | | | | | | | | |
| p-Mentha-1,8-diene | 250 | 100 | 220 | 213 | 185 | 110 | 85 | — |
| p-Menth-1-ene-8,9-diol | 250 | 100 | 176 | 168 | 122 | 65 | 41 | — |
| 9-Acetoxy-p-menth-1-en-8-ol | 310 | 100 | 395 | 457 | 534 | 464 | 277 | 157 |
| 9-Propionyloxy-p-menth-1-en-8-ol | 330 | 100 | 322 | 497 | 472 | 402 | 367 | 324 |
| Known choleretics: | | | | | | | | |
| Felicur | 50 | 100 | 231 | 230 | 188 | 147 | — | — |

*The mean volume of the bile secreted for one hour before the drug administration wad 1798 μl, which was defined as 100 %.

From the above results, it is evident that the choleretics of the present invention increase the volume of the bile secretion 2–5 times larger than that before the drug administration, and were of long duration of choleretic action. In addition, the volume of the bile secreted is roughly proportional to the doses administered.

Since the choleretics of the present invention are usually given via an oral route, it is important to carry out the toxicity test on the limonene derivatives, which are effective ingredients of the choleretics of the present invention. Their acute toxicity as well as their effects on the metabolism function of the liver were investigated, and the high safety was ensured for medical use.

Acute toxicity test

The test drugs were suspended in 5% gum arabic aqueous solution to make 50 mg/ml, and given orally male mice of ddY strain weighing 18–22 g and male rats of Wistar strain weighing 95–120 g. The $LD_{50}$ values were calculated from the mortality of the animals that ensued during the 72 hours following the drug administration The results were shown in Table 3.

Table 3

Acute toxicity in mice and rats

| Choleretics of the present invention | $LD_{50}$ values (mg/kg) | |
|---|---|---|
| | mice | rats |
| p-Mentha-1,8-diene | 5600 (4800–6500) | 4400 (3400–5900) |
| p-Menth-1-ene-8,9-diol | 1800 (1500–2160) | — |
| 9-Acetoxy-p-mentha-1-en-8-ol | 1000–2000 | 8300 (6860–10040) |
| 9-Propionyloxy-p-menth-1-en-8-ol | more than 4000 | — |

Figures in parentheses indicate 95 % confidence limit.

Effects on the sleeping time induced by hexabarbital

About 500 mg of the test drugs were weighed accurately and suspended in 2 ml of 5% gum arabic aqueous solution. Ten male rats of Wistar strain were used per group and given orally the test drugs prepared above in a volume of 0.1 ml/100 g body weight (equivalent to 250 mg/kg), once daily (at 8.30–9.00 a.m.), for a week. The animals were fasted overnight after the last administration of the test drugs. Subsequently, 10% hexobarbital sodium aqueous solution was injected intraperitoneally in a volume of 0.1 ml (equivalent to 100 mg/kg) and the sleeping time was measured. The animals were regarded as sleeping when the loss of righting reflex persist for more than 30 seconds.

The results were shown in Table 4.

Table 4

Effects on the sleeping time induced by hexobarbital

| Test drugs | Sleeping time (minutes) |
|---|---|
| Control | 17.1 ± 0.9 |
| p-Menth-1-ene-8,9-diol | 17.8 ± 0.3 |
| 9-Acetoxy-p-menth-1-en-8-ol | 18.1 ± 1.5 |

From the above results, it is evident that the choleretics of the present invention have extremely low toxicity, and in addition, little or no effects on the metabolism function of the liver. Thus, it may be said that the said choleretics of high biological safety are suitable for oral use. The medical use of the said limonene derivatives, which are effective ingredients of the choleretics of the present invention, have not been found in any publications. Furthermore, the said limonene derivatives may be useful as medicines from the industrial standpoint, possessing marked choleretic activities and ensuring a high biological safety as shown in the above bile secretion and toxicity tests.

Some of the preferred embodiments of the present invention are disclosed in the following examples, but it is not intended that these examples shall be construed to limit the scope of the present invention.

EXAMPLE 1

About 500 mg of p-menth-1-ene-8,9-diol were weighed accurately, and suspended in 10 ml of 5% gum arabic aqueous solution. This suspension was used as a choleretic of the present invention. Male rats of Wistar strain weighing 200 g were fasted overnight, anesthetized by subcutanous injection of 0.3 g of urethane and laparotomized. A polyethylene tube was inserted into the common bile duct. The bile was collected for one hour from 30 minutes after the operation. Subsequently, 1 ml of the choleretic of the present invention (250 mg/kg) was administered orally. The volume of the bile secreted for the first, second and third one hour after the drug administration were 2.1, 1.7 and 1.2 times larger, respectively, than that secreted for one hour before the drug administration.

EXAMPLE 2

About 500 mg of 9-acetoxy-p-menth-1-en-8-ol was weighed accurately and suspended in 10ml of 5% gum arabic aqueous solution. This suspension was used as a choleretic of the present invention. Male rats of Wistar strain weighing about 210 g were fasted overnight and anesthetized by subcutaneous injection of 0.32 g of urethane and then laparotomized. A polyethylene tube was inserted into the common bile duct, and the bile secreted through the duct was collected for one hour from 30 minutes after the operation. Subsequently, the choleretic of the present invention was administered orally in a volume of 1.05 ml (250 mg/kg). The volume of the bile secreted for the first, second and third one hour after the drug administration were 1.9, 1.7 and 1.4 times larger, respectively, than that secreted for one hour before the drug administration.

EXAMPLE 3

About 2.5 g of p-mentha-1,8-diene was weighed accurately and suspended in 50 ml of 5% gum arabic aqueous solution. This suspension was used as a choleretic of the present invention. A male mongrel dog weighing 8.8 kg was fasted overnight and anesthetized by subcutaneous injection of 1.0 mg/kg of urethane and laparotomized. One canula was inserted into the common bile duct and directed to the liver for collection of the bile, and the other canula was also inserted into the duodenum for the drug administration. Subsequently, the cholecystic duct was ligated and the gallbladder bile was aspirated with an injection syringe. The operation was finished after suturing the peritoneum. The bile was collected for one hour from 30 minutes after the operation, and subsequently, 44 ml of the test drug prepared above (250 mg/kg) was given through the canula for the drug administration. The volume of the bile secreted for the first, second and third one hour after the drug administration were 2.2, 2.1 and 1.9 times larger, respectively, than that secreted for one hour before the drug administration.

EXAMPLE 4

About 2.5 g of 9-propionyloxy-p-menth-1-en-8-ol was weighed accurately and suspended in 50 ml of 5% gum arabic aqueous solution. This suspension was used as a choleretic of the present invention. A male mongrel dog weighing 7.6 kg was fasted overnight and anesthetized by subcutaneous injection of 1.0 mg/kg of urethane and then laparotomized. One canula was inserted into the common bile duct and directed to the liver for collection of the bile, and the other canula into the duodenum for the drug administration. Subsequently, the cholecystic duct was ligated and the gallbladder bile was aspirated with an injection syringe. The operation was finished by suturing the peritoneum. The bile was collected for one hour from 30 minutes after the operation, and 50 ml (330 mg/kg) of the test drug prepared above was administered through the canula for the drug administration. The volume of the bile secreted for the first, second and third one hour after the drug administration was 3.2, 5.0 and 4.7 times larger, respectively, than that secreted for one hour before the drug administration.

What we claim is:

1. A choleretic pharmaceutical composition comprising a choleretic amount of one or more limonene derivatives selected from the group consisting of 9-acetoxy-p-menth-1-en-8-ol and 9-propionyloxy-p-menth-1-en-8-ol, as effective ingredients, and a pharmaceutically acceptable excipient, wherein said composition is in the form of a capsule, granule, pill, powder, tablet, syrup or rectal suppository.

2. The composition of claim 1 wherein the effective ingredient consists of 9-acetoxy-p-menth-1-en-8-ol.

3. The composition of claim 1 wherein the effective ingredient consists of 9-propionyloxy-p-menth-1-en-8-ol.

4. A method for increasing the volume of bile secreted by a patient, comprising administering to the patient, internally, an amount sufficient to increase the volume of bile secreted of the choleretic pharmaceutical composition of claim 1.

5. A method in accordance with claim 4 wherein said administration is oral administration.

6. A method in accordance with claim 5, wherein said effective ingredient is 9-acetoxy-p-menth-1-en-8-ol.

7. A method in accordance with claim 4, wherein said patient is a human and said limonene derivatives are administered in a dosage of 150–2500 mg/day.

8. A method in accordance with claim 7, wherein said effective ingredient is 9-acetoxy-p-menth-1-en-8-ol.

9. A method in accordance with claim 4, wherein said patient has a hepato-biliary disease treatable by a bile volume increasing choleretic.

10. A method in accordance with claim 9, wherein said effective ingredient is 9-acetoxy-p-menth-1-en-8-ol.

11. A method in accordance with claim 4, wherein said effective ingredient is 9-acetoxy-p-menth-1-en-8-ol.

12. A method for increasing the volume of bile secreted by a patient, comprising administering to the patient, internally, an amount sufficient to increase the volume of bile secreted of one or more limonene derivatives selected from the group consisting of 9-acetoxy-p-menth-1-en-8-ol and 9-propionyloxy-p-menth-1-en-8-ol.

13. A method in accordance with claim 12, wherein said patient is a human and said limonene derivatives are administered in a dosage of 150–2500 mg/day.

14. A method in accordance with claim 13, wherein said limonene derivative is 9-acetoxy-p-menth-1-en-8-ol.

15. A method in accordance with claim 12, wherein said patient has a hepato-biliary disease treatable by a bile volume increasing choleretic.

16. A method in accordance with claim 15, wherein said limonene derivative is 9-acetoxy-p-menth-1-en-8-ol.

17. A method in accordance with claim 12 wherein said administration is oral administration.

18. A method in accordance with claim 17, wherein said limonene derivative is 9-acetoxy-p-menth-1-en-8-ol.

19. A method in accordance with claim 12, wherein said limonene derivative is 9-acetoxy-p-menth-1-en-8-ol.

* * * * *